United States Patent
Talbot et al.

(10) Patent No.: US 9,919,147 B2
(45) Date of Patent: Mar. 20, 2018

(54) ELECTRODE ARRAYS AND THEIR LEAD FOR USE IN BIOMEDICAL IMPLANTS

(71) Applicant: Second Sight Medical Products, Inc., San Fernando, CA (US)

(72) Inventors: Neil H Talbot, La Crescenta, CA (US); Jordan M Neysmith, Pasadena, CA (US); Dustin Tobey, Glendora, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 14/219,807

(22) Filed: Mar. 19, 2014

(65) Prior Publication Data
US 2015/0265831 A1    Sep. 24, 2015

(51) Int. Cl.
| | | |
|---|---|---|
| *H01L 23/48* | (2006.01) | |
| *H01L 23/52* | (2006.01) | |
| *H01L 29/40* | (2006.01) | |
| *A61N 1/05* | (2006.01) | |
| *A61N 1/36* | (2006.01) | |
| *A61N 1/375* | (2006.01) | |

(52) U.S. Cl.
CPC ....... *A61N 1/0543* (2013.01); *A61N 1/36046* (2013.01); *A61N 1/375* (2013.01)

(58) Field of Classification Search
CPC ........................................................ A61N 1/05
See application file for complete search history.

(56) References Cited

U.S. PATENT DOCUMENTS

| | | |
|---|---|---|
| 4,628,933 A | 3/1986 | Michelson |
| 4,573,481 A | 12/1986 | Bullara |
| 4,837,049 A | 6/1989 | Byers et al. |
| 5,109,844 A | 5/1992 | de Juan, Jr. et al. |
| 5,215,088 A | 6/1993 | Normann et al. |
| 5,935,155 A | 8/1999 | Humayun et al. |
| 6,400,989 B1 | 6/2002 | Eckmiller |
| 6,458,157 B1 | 10/2002 | Suaning |
| 6,980,462 B1 * | 12/2005 | Ramesh ................. G11C 5/063 257/E27.081 |
| 2003/0071360 A1 * | 4/2003 | Tsai ...................... H01P 11/003 257/759 |
| 2008/0027510 A1 * | 1/2008 | McClure .............. A61N 1/3787 607/54 |
| 2008/0085376 A1 * | 4/2008 | Laude ................. C23C 18/1608 427/554 |
| 2009/0264972 A1 * | 10/2009 | Zhou .................... A61N 1/0543 607/116 |
| 2009/0302445 A1 * | 12/2009 | Pagaila ............... H01L 23/3121 257/678 |
| 2011/0101524 A1 * | 5/2011 | Camacho ............ H01L 21/6835 257/737 |
| 2013/0165990 A1 * | 6/2013 | Mathur .................. A61B 18/18 607/44 |

* cited by examiner

*Primary Examiner* — Ismail Muse
(74) *Attorney, Agent, or Firm* — Scott Dunbar

(57) ABSTRACT

Electrode arrays for biological implants are disclosed. Electrodes are arranged in such a way so that electrical traces overlap other electrical traces in a separate layer without X shaped crossing, while overlapping to a degree sufficient to prevent dielectric breakdown of the insulating, separating layer.

16 Claims, 7 Drawing Sheets

ELECTRODE ARRAYS AND THEIR LEAD FOR USE IN BIOMEDICAL IMPLANTS

TECHNICAL FIELD

The present disclosure relates to neural implants, particularly visual. More particularly, it relates to electrode arrays and their leads for use in biological implants.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, an electrode array is described, the electrode array comprising: a first insulating layer; a first plurality of electrical traces on one surface of the insulating layer, wherein the electrical traces in the first plurality are electrically separated from one another; a second insulating layer, substantially covering the first plurality of electrical traces; a second plurality of electrical traces on the second insulating layer, wherein the second plurality of electrical traces is on an opposite side of the second insulating layer relative to the first plurality of electrical traces; and a third insulating layer, substantially covering the second plurality of electrical traces, wherein a wherein when a first trace of the first plurality of electrical traces is overlapped by a second trace of the second plurality of electrical traces, the first and second trace run overlapping in parallel for a portion of their respective lengths.

DETAILED DESCRIPTION

Figure 1A:
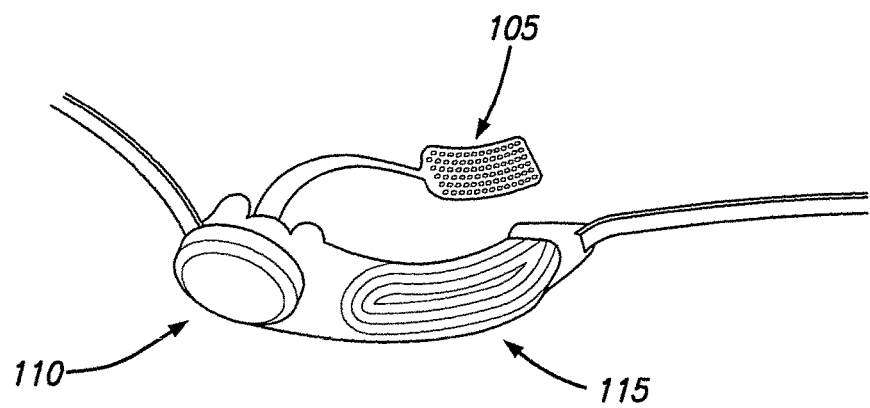
FIGS. 1A-1C illustrate an overview of one embodiment of visual implant.
Figure 1B:
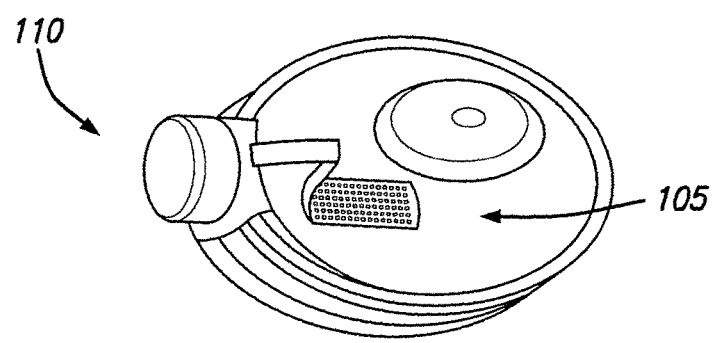
Figure 1C:
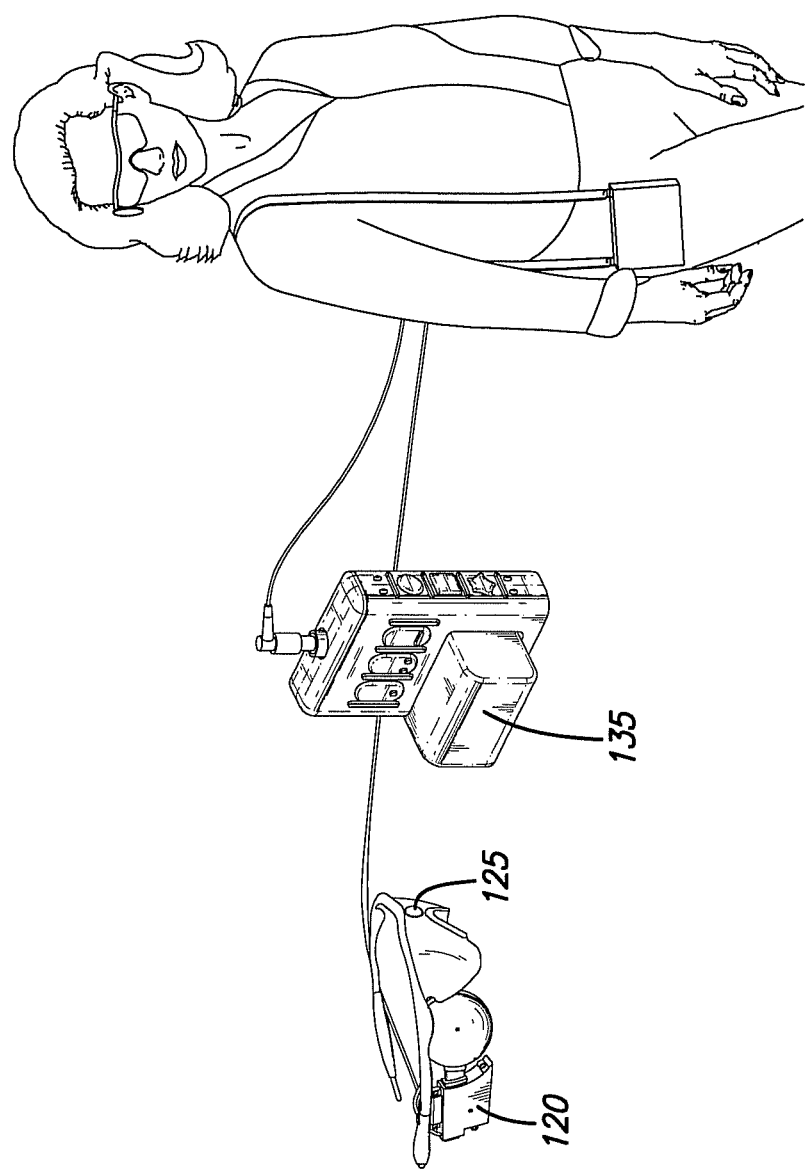

Biological implants, such as ocular implants to be attached to the human retina or other neural interface devices, often comprise a set of electronic components which may control and monitor the function of the implant, and the neural interfacing component itself, usually an array of electrodes. While described here in terms of an electrode array to be attached to the retina for a visual prosthesis, the present disclosure is equally applicable for an electrode array to attached to the visual cortex for a visual prosthesis, a spinal cord stimulator, a deep brain stimulator, a cortical or peripheral nerve interface (stimulator or recorder) for a motor prosthesis, or a wide range of other neural interface devices. For example, in the Second Sight Argus II Retinal Prosthesis, the implant comprises, as visible in FIGS. 1A-1C, an electrode array (105) to be attached to the retina, an electronics case (110) containing electronic components, and an antenna (115) to communicate with the antenna (120) external to the human body.

The external antenna (120) and a camera (125) may be attached to glasses (130) and a control unit (135).

The electrode array is elongated and may be fabricated monolithically with the cable or lead that connects to the rest of the implant. Henceforth the term "electrode array" will be intended to include the cable as well. The electrode array (105) comprises a number of electrical traces which may follow different pattern designs. In one embodiment, the electrical traces run on multiple layers on top of one another. For example, a layer of electrical traces may follow a certain arrangement, and a second layer of electrical traces have its own arrangement, with the two layers being separated by a thin layer of dielectric material so as to achieve electrical insulation.

Obviously the implant needs to be kept down to a small size so as to be implanted in the human body. In addition, the electrode array typically needs to have a degree of flexibility; therefore, the thickness of the dielectric layer between layers of electrical traces may be small. Electrostatic discharge may then occur between two electrical traces on different layers, and if intense enough, dielectric breakdown may occur, with consequence failure of electrode channels.

In fact, electrostatic discharge between different layers of electrical traces can be a major source of yield loss during fabrication of implants.

The present disclosure describes how the electrical traces of implants can be arranged so as to reduce the occurrence of dielectric breakdown.

One possible reason for the dielectric breakdown would be limited overlap between electric traces. For example, two traces could cross in an X pattern and have limited overlap. A difference in electrostatic potential between the traces will have to dissipate over a very small area, resulting in a breakdown of the insulation.

In a no-crossover array, there can be traces that overlap, but the traces overlap over a larger area, for example, several millimeters. This increased overlap allows for a more distributed dissipation of electrostatic charge. Because the electrostatic discharge is so spread out, it does not cause a break down in the insulating layer between traces.

In other words, the layout of the electrical traces in the array either avoids traces from different layers crossing over each other altogether, or for traces that must overlap, they are designed to overlap for a significant portion of their length.

Figure 2A:
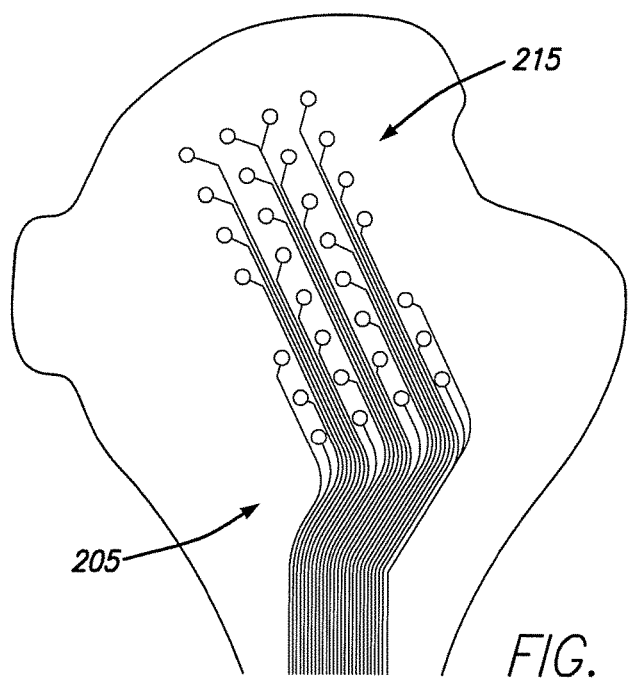
FIGS. 2A-3B illustrate an example of an electrode array with X crossovers.
Figure 2B:
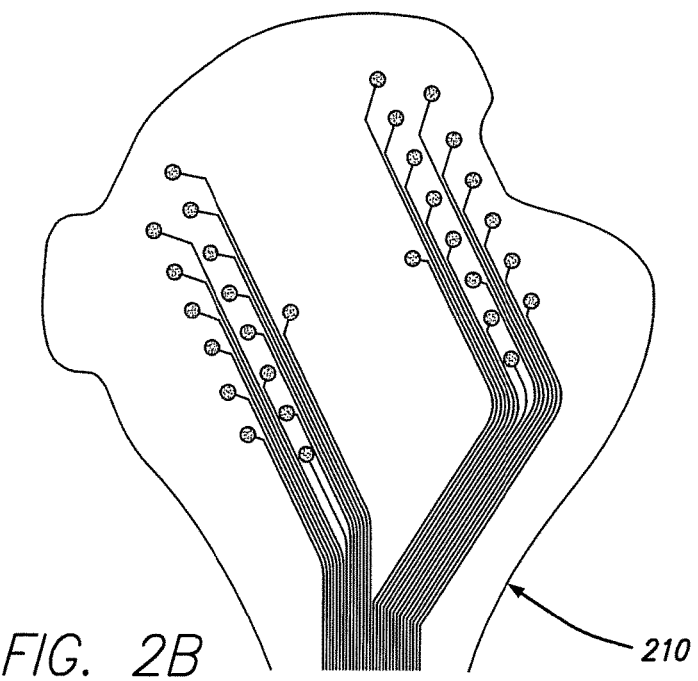

For example, in the Argus II implant, an array may contain 60 thin platinum traces that connect the electrodes to the bond pads. Referring to FIGS. 2A-2B, half (i.e., 30) of the traces are on one layer of polyimide (205) and the other half on a second layer of polyimide (210). Each trace in FIGS. 2A-2B connects to one circular electrode (215).

Figure 3A:
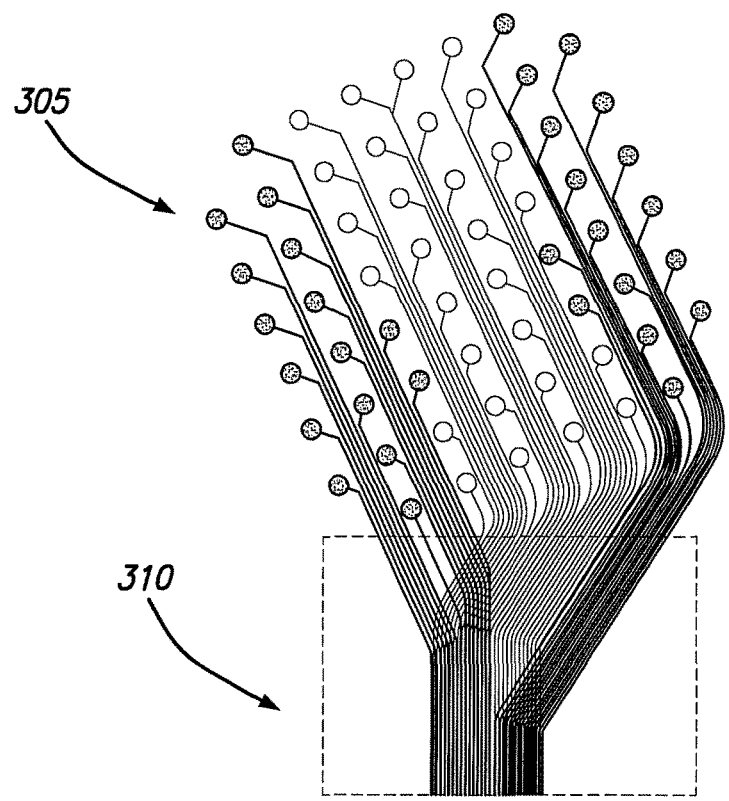
Figure 3B:
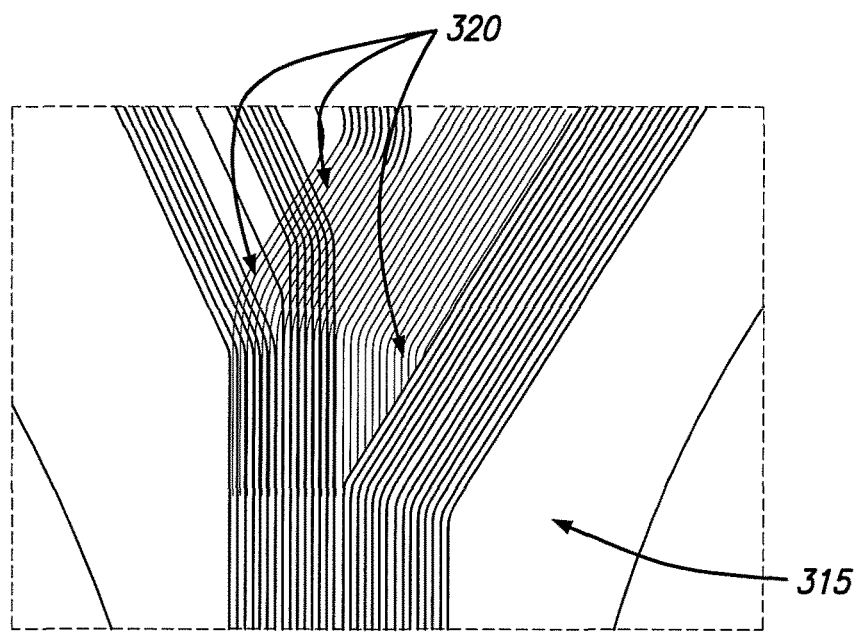

The two layers (205, 210) are separated by a 0.6 μm polyimide dielectric. However, the person skilled in the art will understand that different thicknesses or materials may be used. The metal in each layer is continuous with no layer-to-layer vias. As visible in FIGS. 3A-3B, when superposing the two layers (205, 210), the traces in layer (205) and those in layer (210) cross over each other at 206 locations concentrated near the electrode and bond pad ends of the array. The superposed traces are visible in an overview illustration (305), of which a section (310) is enlarged (315). In the enlarged view (315), the crossover regions (320) are visible, where traces cross over each other. These overlapping intersections (320) between the two metal layers (which form an "X" pattern in-plane) have been found to be more susceptible to shorting due to accidental electrostatic discharge (ESD) events during handling of the array in manufacturing. All arrays and final devices undergo 100% electrical testing to detect shorts or other defects. If interlayer shorts are found, the electrodes associated with the affected trace pairs are disabled. In those cases where the number of disabled electrodes and their location in the array do not meet specification, the devices are rejected.

As a means of reducing the occurrence of interlayer shorts, the traces in the array design of the preset disclosure have been re-routed such that no trace-crossovers occur. As a product of this layout change, some of the intra-layer trace spacings may be increased. In some embodiments, the trace spacing in the crossover regions is 25 µm. In some embodiments, the intra-layer trace spacing ranges from 25 µm to 100 µm. Different thicknesses outside this range may also be used.

Figure 4A:
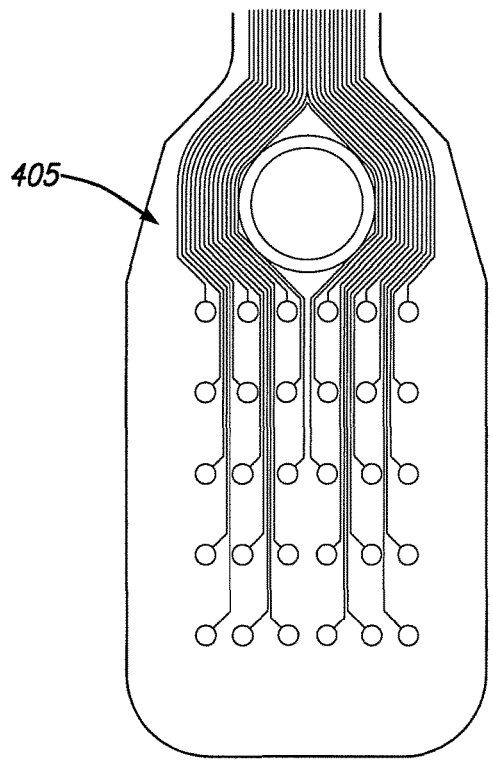
FIGS. 4A-5B illustrate an example of an electrode array with Y crossovers.
Figure 4B:
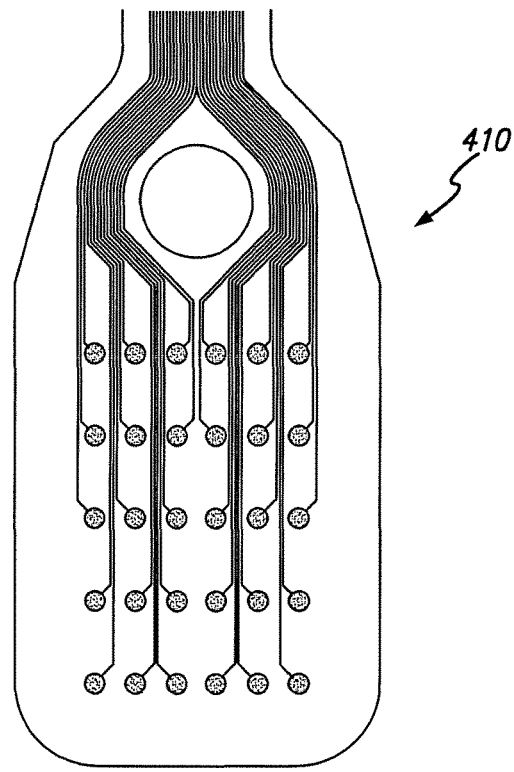
Figure 5A:
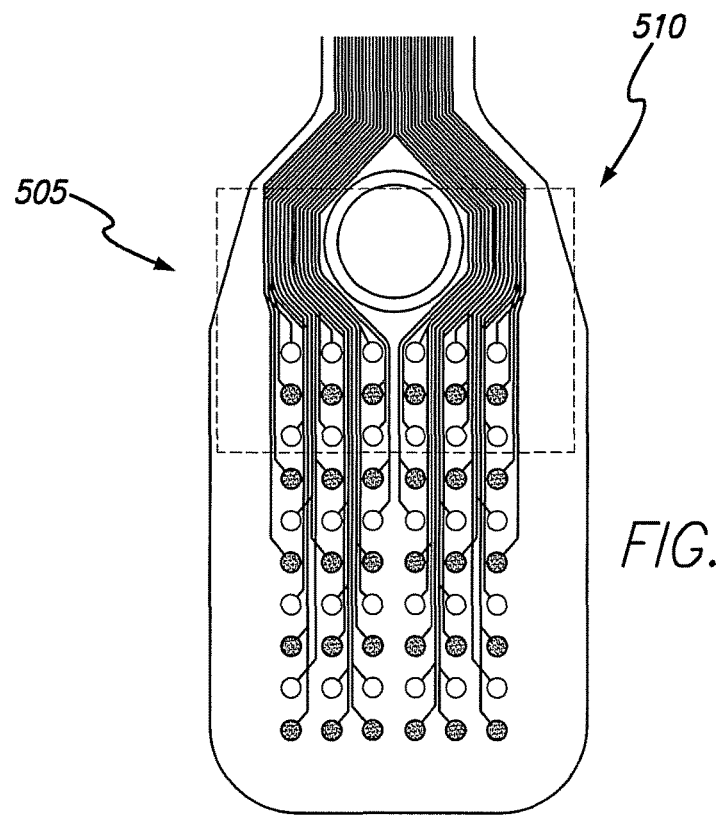
Figure 5B:
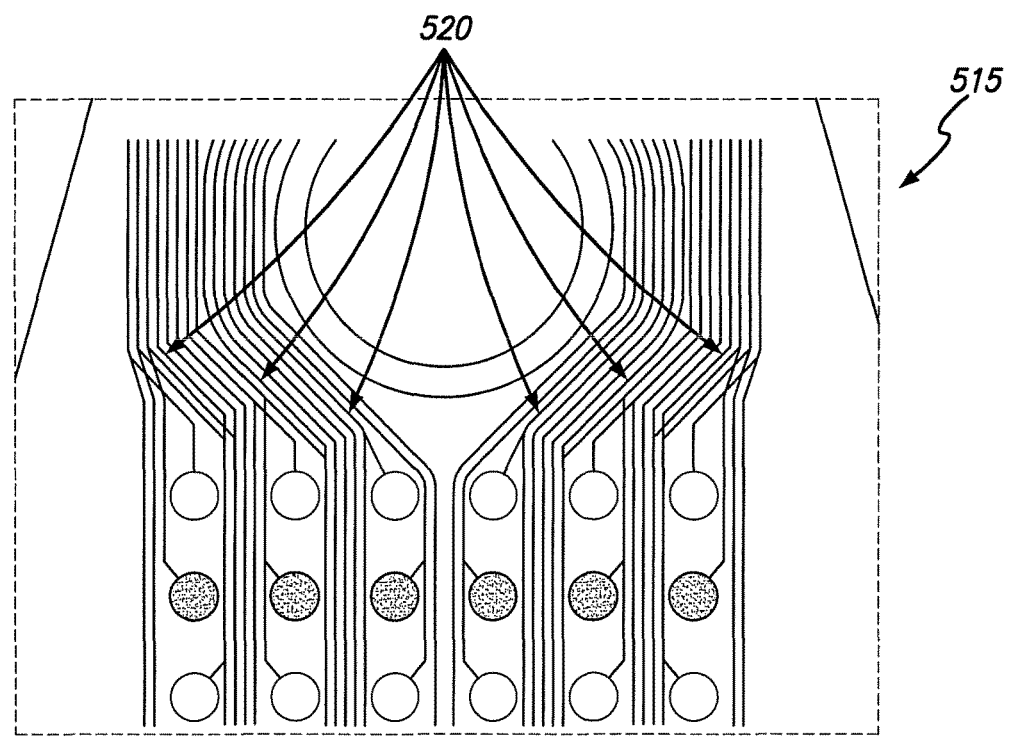

FIGS. 4A-4B illustrate an exemplary embodiment of traces in one layer (405) and a second layer (410). The two layers (405, 410) are superimposed as visible in FIGS. 5A-5B, in the overview pattern (505). A region (510) of the pattern (505) is enlarged in (515). In (515), the crossover regions (520) between traces are illustrated.

The traces overlap in a Y pattern rather than an X pattern. Thereby, the traces from one layer overlap the traces from another layer after the Y overlap region. In some embodiments, the traces overlap for a length greater than half their total length.

The metal traces are etched into discrete conductors using a photolithographic process.

Figure 6:
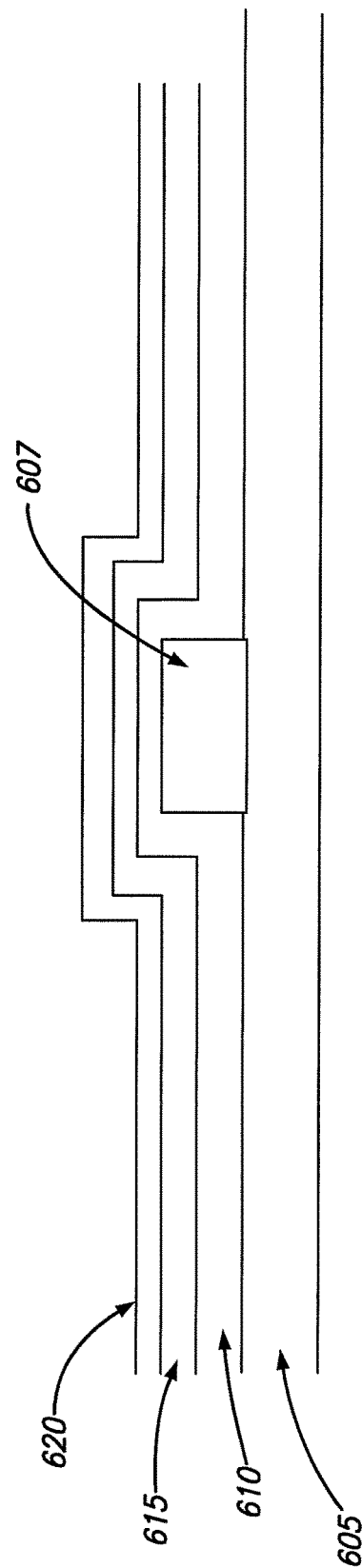
FIG. 6 illustrates an exemplary crossover region cross-section.

FIG. 6 illustrates an exemplary embodiment of a crossover region between two metal traces on different layers. A first platinum trace (607) is deposited on a polyimide dielectric layer (605). The person skilled in the art will understand that different materials may be used.

A second platinum trace (615) is separated from the first trace (607) by a polyimide layer (610). A further polyimide layer (620) covers the second trace (615). As visible in FIG. 6, the cross over region can be referred to as conformal. Some varieties of polymer do not planarize. Such polymers follow the underlying shape to which they are applied to in a conformal manner. In some embodiments of the present disclosure, the trace (607) and the trace (615) do not cross over at a 90 degree angle, but at an angle smaller than 90 degrees.

As understood by the person skilled in the art, the traces described in the present disclosure comprise, in one embodiment, a second subset of electrical traces from the upper plane overlap the first subset of traces in the lower plane forming a Y pattern at the beginning of the overlap, and the first and second subsets run overlapping for a significant fraction of their respective lengths. While the present disclosure is illustrated in an array with two layers of traces, the invention is equally applicable to electrode arrays with three or more layers of traces.

In some embodiments, the traces overlap for a length that is less than 5% of either their respective lengths.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. An electrode array comprising:
a first insulating layer;
a first plurality of electrical traces on one surface of the first insulating layer, wherein the electrical traces in the first plurality of electrical traces are electrically separated from one another;
a second insulating layer, substantially covering the first plurality of electrical traces;
a second plurality of electrical traces on the second insulating layer, wherein the second plurality of electrical traces is on an opposite side of the second insulating layer relative to the first plurality of electrical traces, and wherein the electrical traces in the second plurality of electrical traces are electrically separated from one another;
a third insulating layer, substantially covering the second plurality of electrical traces,
wherein the first plurality of electrical traces and the second plurality of electrical traces connect bond pads on a first end with electrodes on a second end; and
wherein at least one trace of the first plurality of electrical traces crosses over at least one trace of the second plurality of electrical traces and wherein the one trace of the first plurality of electrical traces and the one trace of the second plurality of electrical traces run overlapping and parallel, for a portion of their respective lengths.

2. The electrode array of claim 1, wherein the first, second and third insulating layers are made of polyimide.

3. The electrode array of claim 1, wherein the first and second plurality of electrical traces are made of platinum.

4. The electrode array of claim 1, wherein the thickness of the second insulating layer is between 0.1 µm and 10 µm.

5. The electrode array of claim 1, wherein the thickness of the first and third insulating layer is between 1 µm and 50 µm.

6. The electrode array of claim 1, wherein each insulating layer above another insulating layer conformally covers the insulating layer below it.

7. The electrode array of claim 1, further comprising a third plurality of electrical traces on the third insulating layer, wherein the third plurality of electrical traces is on an opposite side of the third insulating layer relative to the second plurality of electrical traces; and
a fourth insulating layer, substantially covering the third plurality of electrical traces.

8. The electrode array of claim 7, wherein the thickness of the second and third insulating layers are between 0.1 µm and 10 µm.

9. The electrode array of claim 7, wherein the thickness of the first and fourth insulating layers are between 1 µm and 50 µm.

10. An apparatus comprising:
the electrode array of claim 1; and
an electronics case controlling the electrode array, wherein the electrode array is connected to the electronics case through an electrical cable.

11. The apparatus of claim 10, wherein the electrical cable is fabricated monolithically with the electrode array.

12. The apparatus of claim 10, further comprising an internal antenna connected to the electronics case.

13. The apparatus of claim 12, wherein the electrode array is configured to be attached to a human retina, and the electronics case and the internal antenna are configured to be attached to a human eye.

14. The apparatus of claim 13, further comprising:
an external antenna, configured to communicate with the internal antenna; and
a camera, configured to transmit information to the electronics case through the external and the internal antenna.

15. The apparatus of claim 14, further comprising a glasses, wherein the glasses is configured to support the external antenna and the camera.

16. The electrode array of claim 1, wherein the length of the portion of the one trace of the first plurality of electrical traces and the one trace of the second plurality of electrical traces which is overlapping is less than 5% of the length of either the first or the second trace.

* * * * *